United States Patent
Zaytoun, Jr.

(10) Patent No.: US 8,443,480 B2
(45) Date of Patent: May 21, 2013

(54) OSTOMY POUCH CLEANER

(76) Inventor: George R. Zaytoun, Jr., New Bern, NC (US)

( * ) Notice: Subject to any disclaimer, the term of this patent is extended or adjusted under 35 U.S.C. 154(b) by 300 days.

(21) Appl. No.: 12/925,358

(22) Filed: Oct. 20, 2010

(65) Prior Publication Data

US 2012/0097186 A1   Apr. 26, 2012

(51) Int. Cl.
*B08B 9/00* (2006.01)
*B08B 1/00* (2006.01)

(52) U.S. Cl.
USPC .......................................... 15/210.1; 15/211

(58) Field of Classification Search
USPC .............. 15/104.94, 209.1, 210.1, 211; 604/1
See application file for complete search history.

(56) References Cited

U.S. PATENT DOCUMENTS

| | | | |
|---|---|---|---|
| 2,610,347 A * | 9/1952 | Kleiner | 15/210.1 |
| 4,075,033 A | 2/1978 | Knox et al. | |
| 5,067,194 A | 11/1991 | Rosenfeld et al. | |
| 5,875,512 A | 3/1999 | Lathan | |
| 6,158,077 A | 12/2000 | Wenger et al. | |
| 6,269,516 B1 | 8/2001 | Saatjian et al. | |
| 7,424,764 B2 * | 9/2008 | Trenz et al. | 15/210.1 |

FOREIGN PATENT DOCUMENTS

| | | | |
|---|---|---|---|
| JP | 8-112219 | * | 5/1996 |
| JP | 10-43092 | * | 2/1998 |
| JP | 10-108804 | * | 4/1998 |

* cited by examiner

*Primary Examiner* — Mark Spisich
(74) *Attorney, Agent, or Firm* — MacCord Mason PLLC

(57) ABSTRACT

A hand tool and related method is provided for cleaning the discharge opening of an ostomy pouch. The hand tool includes a handle with a handgrip, a swab holder, and a bore extending through the handle; and a swab plunger having a telescoping shaft with proximal and distal ends extending though the bore, a gripping member attached to the proximal end of the shaft, and a swab engagement cap attached to the distal end of the shaft, the plunger having retracted and extended positions. A closed-end tubular swab is inserted over the distal end of the swab holder to wipe waste material from the ostomy pouch discharge opening. The plunger is then extended and pushed forward to detach the swab from the hand tool.

13 Claims, 4 Drawing Sheets

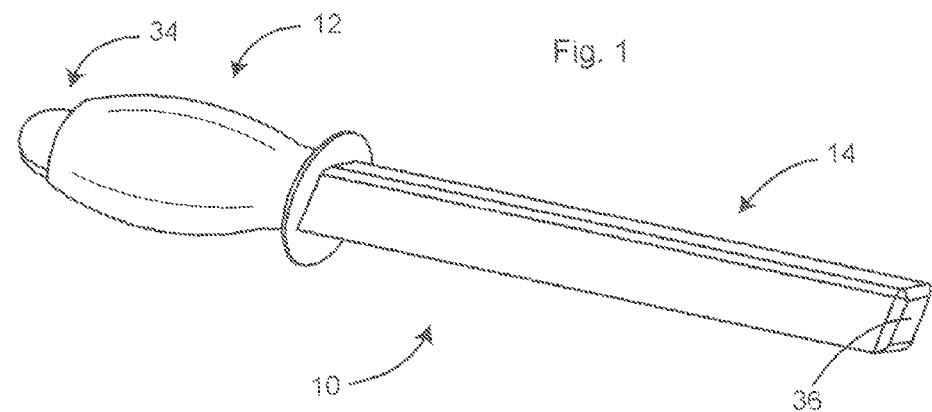
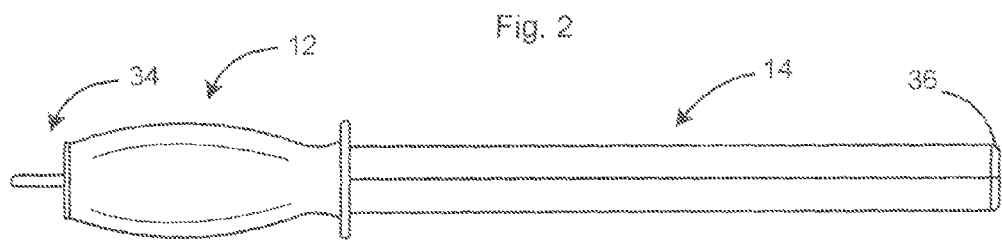
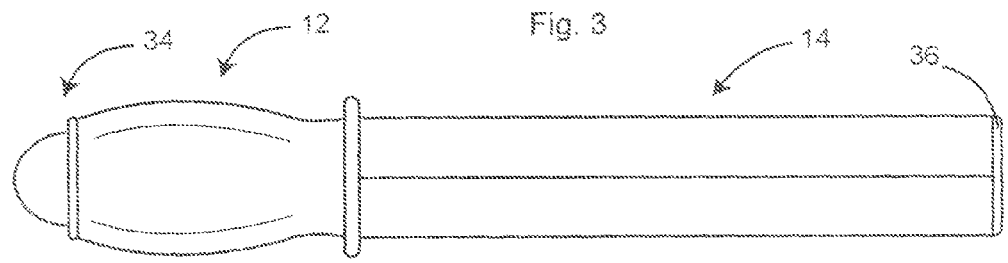

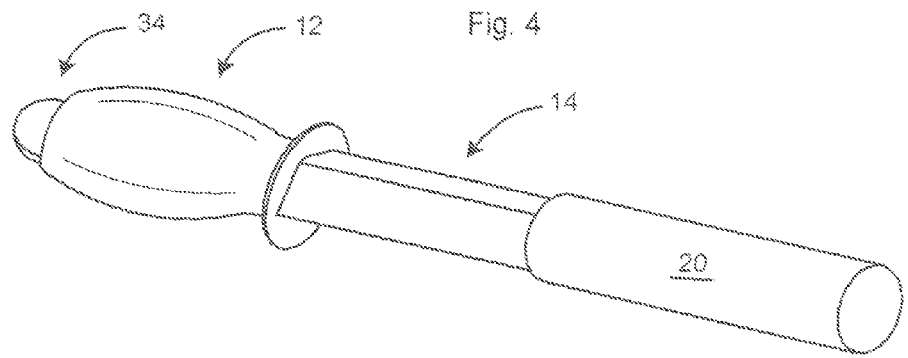
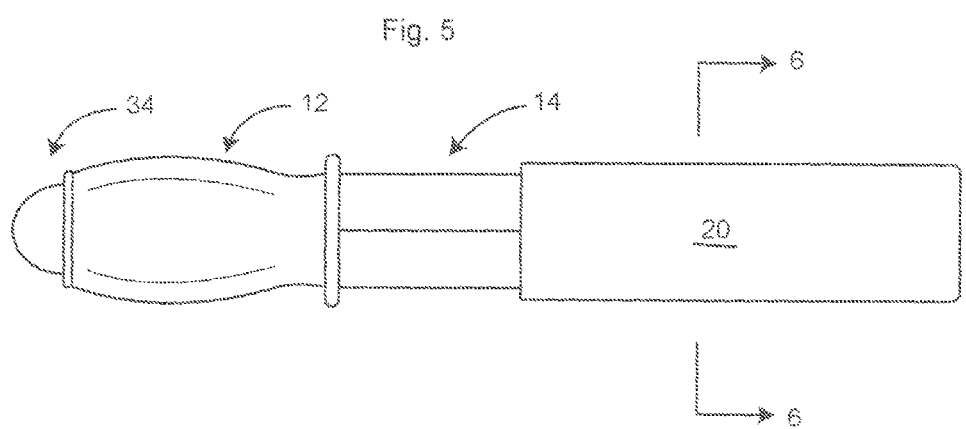
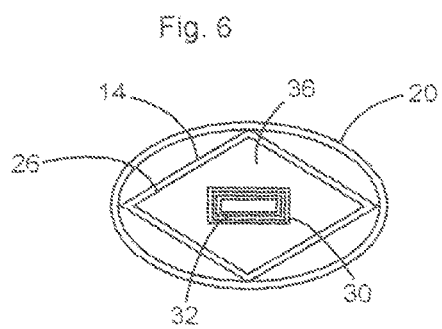

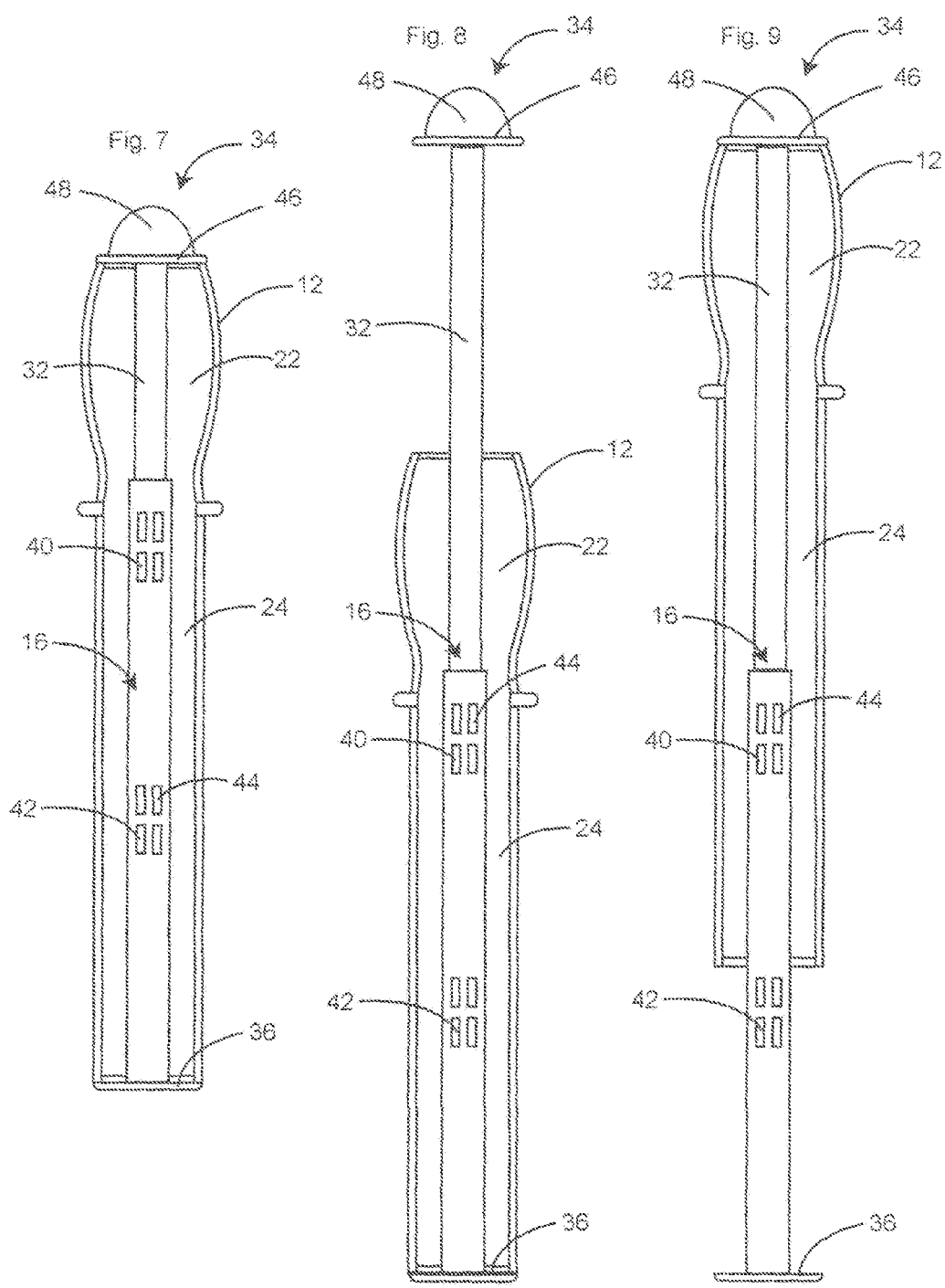

OSTOMY POUCH CLEANER

BACKGROUND OF THE INVENTION (1) Field of the Invention

The present invention relates to a tool for use in cleaning the discharge opening of an ostomy pouch, and in particular to a handheld cleaning tool that includes a disposable cleaning swab that can be discharged from the tool after use without contact by the user's hand.

(2) Description of the Prior Art

A colostomy is a surgical procedure to remove all or part of the colon. It is used to treat many conditions including colon cancer, Crohn's disease, intestinal obstruction, birth defects, and diverticulitis. In the operation, a stoma, or opening, is made in the abdominal wall and the end of the intestine is joined to the opening. Bodily wastes are then excreted and collected into an ostomy pouch, also known as a colostomy bag, attached to the stoma.

There are basically two types of ostomy pouches: open-end pouches that have a resealable end which can be opened to drain the contents of the pouch into a toilet, and closed-end pouches that must be removed and replaced with a new pouch. The present invention relates to open-end ostomy pouches.

An open-end ostomy pouch is comprised of a flat, watertight collection bag or pouch having an entry opening and a discharge opening. The pouch is attached to the user's body with a mounting plate, commonly called a wafer or a baseplate, that is attached around the entry opening. The mounting plate has an adhesive inner surface to secure the plate to the body. The resealable discharge opening of the pouch may be sealed with a plastic clip, or a Velcro-type closure.

When the pouch is to be emptied, the user opens the discharge opening and drains the pouch contents into the toilet. The discharge end of the pouch must then be cleaned before reclosing. Normally, cleaning is done by wiping the inside of the discharge opening with rolled toilet tissue. This procedure is both messy and often incomplete, requiring insertion of the tissue into the discharge opening with the fingers, and attempting to completely swab the discharge opening inner surface with the flexible and easily torn rolled toilet paper.

SUMMARY OF THE INVENTION

The present invention provides a handheld tool for use in cleaning the discharge opening of an ostomy pouch that is an improved alternative to the use of rolled toilet tissue currently used for this purpose. Basically, the tool is comprised of a handgrip, an elongated swab holder extending from the forward end of the handgrip, a swab slidably insertable onto the swab holder, and an extendible plunger to remove the swab from the swab holder after use.

More particularly, the handgrip is a tubular handgrip having a length approximating or slightly greater that the width of an adult's hand, e.g., from about 4 to about 6 inches. The cross-section of the handgrip may be shaped to receive the hand, e.g., the cross-section may be circular or oval. The end of the handgrip may be outwardly flared to prevent the user's hand from slipping from the handgrip. An axial bore extends through the handgrip from the proximal end the distal end.

The elongated swab holder extends outwardly from the distal end of the handgrip, with the proximal end of the swab holder being attached against the distal end of the handgrip. The handgrip and swab holder may be integrally formed, e.g., by molding from a suitable plastic. The handgrip and swab holder may collectively be referred to herein as the handle.

The swab holder has a constant diameter shaped for insertion into the interior of the swab to be described. Preferably, the swab holder has a different cross-sectional shape from the shape of the swab inner cross-section. For example, the swab holder may have a non-circular, e.g, rectangular or diamond shaped cross-section, while the swab cross-section is circular, aiding in the removal of the swab from the swab holder.

The swab holder also includes an axial bore extending between the proximal and distal ends of the swab holder. The swab holder bore is of the same cross-section as the handgrip bore and is aligned with the handgrip bore, forming a continuous bore from the handgrip proximal end to the swab holder distal end. The swab holder is preferably from about 3 to about 6 inches in length.

The swab holder is configured to hold disposable swabs that are inserted over the distal end of the swab holder for use in cleaning the ostomy discharge opening. Generally, the swab is in the shape of a closed end tube having an inner bore with a shape and size corresponding to the exterior dimensions of the swab holder. The swab is formed of an absorbent material, e.g., paper or other cellulosic fiber material, of a foam. The swab is preferable molded. The end cap extends across the distal end of the swab, while the proximal end of the swab is open for insertion of the swab holder.

The swab discharge member is in the form of an extendible plunger moveable within the bore of the handgrip and swab holder for use in pushing the swab off of the swab holder after use. Generally, the plunger is comprised of an extendible shaft having a proximal end and a distal end, a finger grip attached to the proximal end of the shaft, and a swab engagement cap attached to the distal end of the shaft.

The extendible shaft has a retracted state in which the length of the shaft is approximately equal to the combined lengths of the handgrip and swab holder, and an extended state that is equal to or greater than the length of the combined handgrip and swab holder, plus the length of the swab. Thus, the swab is completely pushed from the swab holder when the extended plunger is pushed completely forward.

In a preferred embodiment of the invention, the plunger shaft is a telescoping shaft with an outer tubular section and an inner section slidable within the outer section. One of the sections includes a protrusion that fits into a detent, i.e., a recess or hole, in the other section when the sections are extended.

The finger grip attached to the proximal end of the plunger shaft is shaped to be gripped between the user's thumb and forefinger. Generally, the finger grip includes an end plate transverse to the shaft axis and a gripping plate extending outward from the rear face of the end plate. The gripping plate has opposed, normally flat, surfaces to be contacted with the thumb and forefinger. The end plate has a diameter greater than the diameter of the handgrip bore to prevent the fingergrip from entering the bore. Preferably, the handgrip end plate has the same cross-section as the proximal end of the handgrip.

The swab engagement cap is attached to the distal end of the plunger shaft and is designed to push on the inner surface of the swab end cap to slide the swab off of the swab holder so that the used swab can be dropped into a toilet or other disposal receptacle without being touched by the user. The end cap has a diameter greater than the diameter of the swab holder bore so that the cap cannot be pulled into the bore. The cap diameter is no greater than the diameter of the swab holder, and is preferably less than the inner diameter of the swab so that the used swab will readily drop from the plunger. The cap may be in the form of a flat cap that is transverse to the plunger shaft axis.

The tool is used by inserting a swab onto the swab holder. The length of the swab interior is no greater than the length of the swab holder so that the end cap of the plunger will engage the inner surface of the swab when the swab is fully inserted. The swab and front end of the swab holder are then inserted into the opened discharge end of the ostomy pouch and moved around the inner surface of the pouch opening to remove waste material. After cleaning is completed, the user pulls the finger grip away from the handgrip with one hand while holding the handgrip with the other hand to extend and lock the plunger shaft in its extended position. The finger grip is then moved back toward the handgrip, which moves the end cap away from the distal end of the swab holder, pushing the swab off of the holder. The swab is then permitted to drop from the plunger into the toilet or appropriate receptacle for disposal.

Since waste material does not contact the tool during use, the tool can be reused. The plunger finger grip is pushed toward the end cap to disconnect the latching member and retract the plunger shaft.

BRIEF DESCRIPTION OF THE DRAWINGS

FIG. 1 is a perspective view of the hand tool.
FIG. 2 is a side view of the hand tool.
FIG. 3 is a top view of the hand tool.
FIG. 4 is a perspective view of the hand tool with inserted swab.
FIG. 5 is a top view of the hand tool with inserted swab.
FIG. 6 is a sectional end view of the swab handle as seen along line 6-6 of FIG. 5.
FIG. 7 is a sectional top view of the hand tool with the plunger in the retracted position.
FIG. 8 is a sectional top view of the hand tool with the plunger in the extended rearward position in preparation for pushing of a swab from the swab holder.
FIG. 9 is a sectional top view of the hand tool with the plunger in the extended forward position used to discharge a swab from the swab holder.

DETAILED DESCRIPTION OF THE INVENTION

Figure 10:
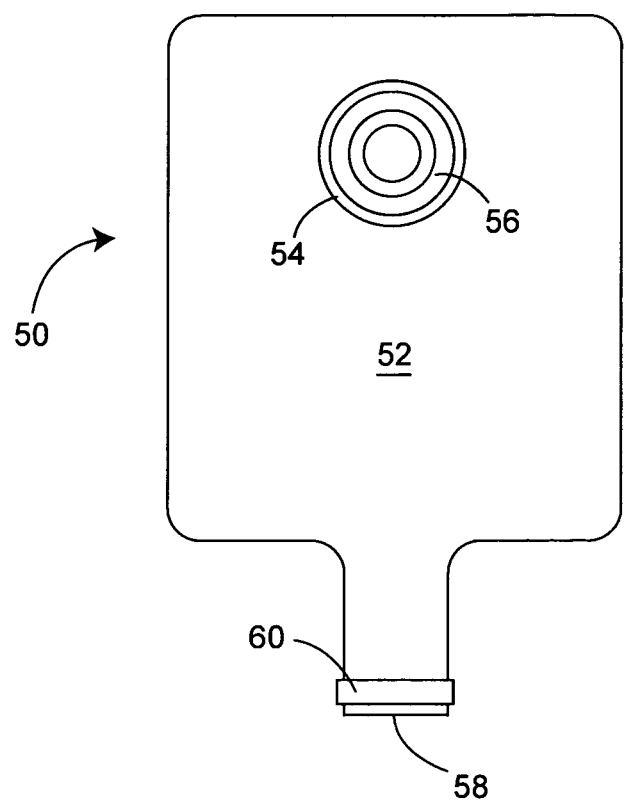
FIG. 10 is a rear view of a typical ostomy pouch.

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

As illustrated in the drawings, a preferred embodiment of the ostomy cleaner hand tool, generally 10, is comprised of a handgrip, generally 12, an elongated swab holder, generally 14, extending from the forward end of handgrip 12, a swab discharge plunger, generally 16, to remove a swab 20, from swab holder 14 after cleaning of a ostomy pouch opening.

More particularly, tubular handgrip 12, which has a length approximating or slightly greater that the width of an adult's hand, includes a proximal end and a distal end. The distal end of the handgrip may be outwardly flared. Axial bore 22 extends through handgrip 12 between its proximal and distal ends.

Elongated swab holder 14 extends outwardly from the distal end of handgrip 12, with the proximal end of swab holder 14 being attached against the distal end of handgrip 12. Handgrip 12 and swab holder 14 may be integrally formed. Swab holder 14 has a constant diameter shaped for insertion into the interior of swab 20. As illustrated in the preferred embodiment, swab holder has a diamond-shaped cross-section to aid in discharge of swab 20. Swab holder 14 also includes an axial bore 24 extending between its proximal and distal ends. Bore 24 is axially aligned with handgrip bore 22, forming a continuous bore for discharge plunger 16.

Swab holder 14 is configured to hold a disposable swab 20, which is in the shape of a closed end tube having an inner bore 26 sized for insertion onto swab holder 14. As shown in the preferred embodiment, inner bore 26 has a circular cross-section. Swab 20 may be formed of molded, absorbent cellulosic fiber material. The closed end of swab 20 cap extends across the distal end of swab 20, while the proximal end of swab 20 is open for insertion of swab holder 14.

Swab discharge plunger 16 is moveable within handgrip bore 22 and swab holder bore 24 to push swab 20 off of swab holder 14 after use. Generally, plunger 16 is comprised of a telescoping shaft having a front section 30 and a rear section 32 slidable within section 30 between a retracted position and an extended position. A finger grip 34 is attached to the proximal end of the shaft section 32, and a swab engagement cap 36 is attached to the distal end of shaft section 30. Section 30 includes two sets of openings 40 and 42 to receive protrusion 44 on shaft section 32, releasibly locking sections 30 and 32 in their retracted or extended positions. It will be understood that the positions of openings and protrusions may be reversed, i.e., section 30 may include protrusions and section 32 may include openings. Alternatively, the sections may include mating protrusions instead of an opening and a protrusion.

Finger grip 34 is shaped to be gripped bets between the user's thumb and forefinger, and includes end plate 46 transverse to the longitudinal axis of handgrip 12 and a gripping plate 48 extending across the proximal end of handgrip 12. Swab engagement cap 36 has a diameter greater than the diameter of the swab holder bore 24 so that cap 36 cannot be pulled into bore 24.

FIGS. 7-9 illustrate hand tool 10 in operation. In FIG. 7, tool 10 is in its closed position for storage. In FIG. 8, plunger 16 is in the extended, rearward position in readiness of discharge of swab 20, not shown. In FIG. 9, extended plunger 16 is pushed fully forward so that cap 36 can pull swab 20 away from holder 14.

FIG. 10 illustrates the rear view of a typical ostomy pouch, generally 50, comprised of a waterproof bag 52, an attachment plate 54 with adhesive ring 56 and discharge opening 58 with closing clip 60.

It will be apparent from the foregoing description that the present invention is also useable in cleaning ostomy pouches used with ileostomies (small intestine) and urostomies (urinary) in addition to colostomies (colon). Also, certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A hand tool to hold a swab for use in cleaning the discharge opening of an ostomy pouch comprising:
   a) a handgrip having a proximal end, a distal end, and a first axial bore extending between said proximal and distal ends;
   b) a swab holder having a proximal end, attached to the distal end of said handgrip, a distal end, and a second axial bore aligned with the first axial bore; and
   c) a swab plunger having an extendible shaft with proximal and distal ends extending though said first and second axial bores, a gripping member attached to the proximal end of said shaft, and a swab engagement cap attached to the distal end of said shaft, said plunger having retracted and extended positions, said extendible shaft being a telescoping shaft having an outer elongated tubular section and an inner elongated section slidable within said outer section between retracted and extended positions, said shaft having releasable locking members engaged at said retracted and extended positions.

2. The hand tool of claim 1, wherein said handgrip and swab holder are integrally formed.

3. The hand tool of claim 1, wherein said swab holder has a non-circular cross-section.

4. The hand tool of claim 1, wherein said gripping member has opposed flat surfaces to be grasped between thumb and forefinger.

5. The hand tool of claim 1, wherein said swab holder is adapted to hold a swab of a given length, the length of said swab plunger being extendable by a length equal to or greater than the given length of said swab.

6. The hand tool of claim 1, wherein the diameter of said swab engagement cap is equal to the cross-sectional diameter of said swab holder.

7. A hand tool for use in cleaning the discharge opening of an ostomy pouch comprising:
   a) a handgrip having a proximal end, a distal end, and a first axial bore extending between said proximal and distal ends;
   b) a swab holder having a proximal end, attached to the distal end of said handgrip, a distal end, and a second axial bore aligned with the first axial bore;
   c) a swab plunger having an extendible shaft with proximal and distal ends extending though said first and second axial bores, a gripping member attached to the proximal end of said shaft, and a swab engagement cap attached to the distal end of said shaft, said plunger having retracted and extended positions, said extendible shaft being a telescoping shaft having an outer elongated tubular section and an inner elongated section slidable within said outer section between retracted and extended positions, said shaft having releasable locking members engaged at said retracted and extended positions; and
   d) a tubular swab insertable over the distal end of said swab holder, said swab having an open proximal end and a closed distal end.

8. The hand tool of claim 7, wherein said handgrip and swab holder are integrally formed.

9. The hand tool in claim 7, wherein said swab holder has a non-circular cross-section.

10. The hand tool of claim 7, wherein said gripping member has opposed flat surfaces to be grasped between thumb and forefinger.

11. The hand tool of claim 7, wherein said swab holder is adapted to hold a swab of a given length, the length of said swab plunger being extendable by a length equal to or greater than the given length of said swab.

12. The hand tool of claim 7, wherein the diameter of said swab engagement cap is equal to the cross-sectional diameter of said swab holder.

13. The hand tool of claim 7, wherein said swab has a circular cross-section.

* * * * *